United States Patent [19]

Fleischer

[11] Patent Number: 4,969,900
[45] Date of Patent: Nov. 13, 1990

[54] MIDDLE EAR PROSTHESIS AND METHOD FOR MOUNTING IT

[76] Inventor: Gerald Fleischer, Am Rosenberg 31, D-6301 Fernwald, Fed. Rep. of Germany

[21] Appl. No.: 159,671

[22] Filed: Feb. 24, 1988

[51] Int. Cl.⁵ .............................................. A61F 2/18
[52] U.S. Cl. .................................................... 623/10
[58] Field of Search .................. 623/11, 10, 12, 16; 128/1 R; 179/107

[56] References Cited

U.S. PATENT DOCUMENTS 4,606,329  8/1986  Hough ................................... 623/10

Primary Examiner—David J. Isabella
Attorney, Agent, or Firm—Fred Philpitt

[57] ABSTRACT

For patients who suffer from a middle ear disease interrupting or destroying the ossicular chain but whose inner ear is intact yet, the invention provides a prosthesis (10) which includes in a casing a complete acoustical transmission system (12, 26, 50) and is adapted to be dismantled following a performance check, then to be mounted stepwise and to be entirely implanted. At the same time, the inflamed middle ear cavity is completely wiped out. Adjacent an inner coupling unit (12) to the oval window (V), there is cover unit (22) or a conduit (24) at the round window (F) of the inner ear. A transfer unit (26) having an artificial tympanic membrane (28) comprises an acoustically transmissive connection (42) to a mastoid unit (50) having a damping insert (54). The outer wall portions (28, 52) of the prosthesis (10) are epithelialized. The transfer unit (26) includes an impedance converter that is partly coated for attenuation, serves to transmit vibrations, permits large pressure intensification and may also be tuned for optimum auditory characteristics.

27 Claims, 6 Drawing Sheets

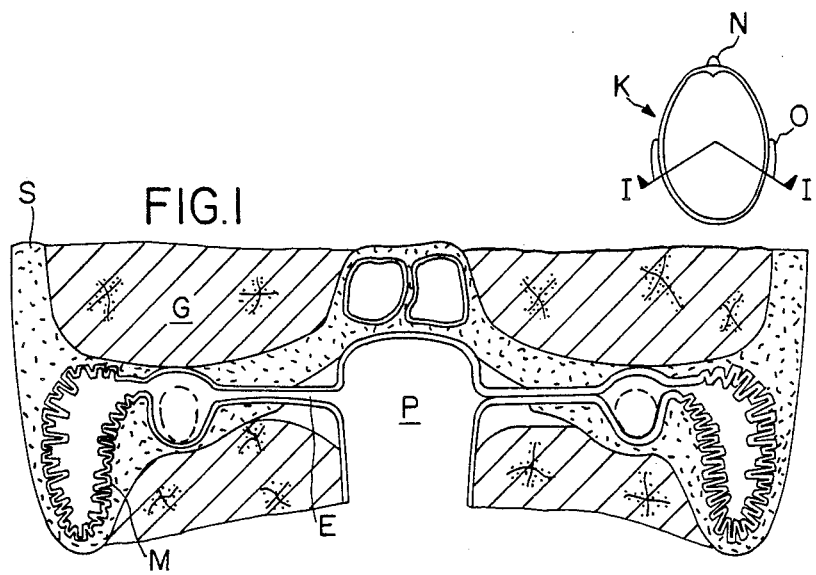
FIG. 1a
FIG. 1
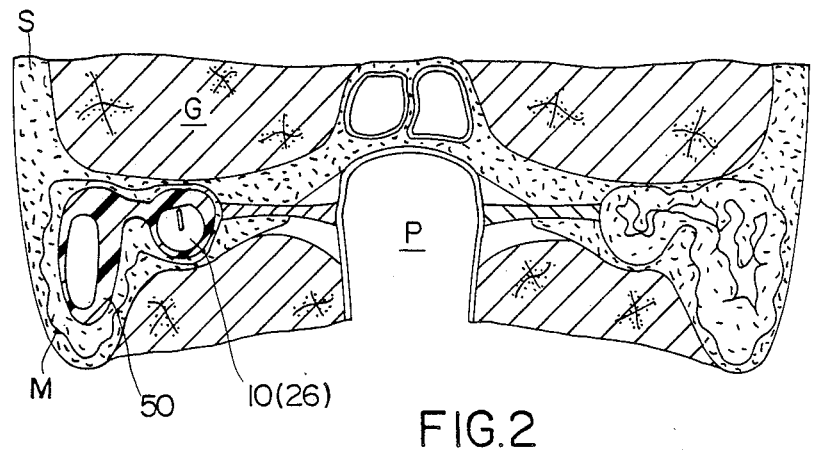
FIG. 2

MIDDLE EAR PROSTHESIS AND METHOD FOR MOUNTING IT

The invention relates to a middle ear prosthesis and to a method for mounting it.

A significantly large number of people suffer from ear diseases ranging from slight reduction of hearing to severe damage. Where hearing capability is lessened only in a general manner, remedy is possible by hearing aids. If particular organ components are damaged or ruined, such as the tympanic membrane or parts of the ossicles, they may be repaired or replaced by artificial component parts. Here, the surgical art has greatly advanced in the last decades.

Examples may be taken from U.S. Pat. Nos. 4,624,672 and 4,281,419 whereby intermediate members such as volute wire springs including several coils or movable shaft joints, respectively, have been proposed for establishing mechanical vibratory links between the tympanic membrane and the stapes. However, such partial reconstruction is possible only where there is still a healthy anchoring system, i.e. where not all of the middle ear has been damaged yet. Unfortunately, though, such severe cases are numerous. Chronical suppuration will not be eliminated by the conventional prostheses.

Proper function of the middle ear depends on ventilation of the tympanic cavity. The air contained therein is partly absorbed by mucous tissue all the time so that it is necessary to supply air and to provide pressure equalization via the Eustachian tube. If the latter becomes clogged and if the mucous membrane is prone to be affected, this may result in repeated disease of the middle ear and even in chronicity. The consequence is a series of pathological processes frequently followed, despite surgical operations, by the loss of the entire mechanism of acoustic transmission to the inner ear. The stapes or its footplate only may be retained. When suppurations in the osseous wall of the middle ear, particularly in the mastoid cavity system (see FIGS. 1 and 2), are removed surgically, the so-called radical cavity is formed which is an enlarged midlle ear volume in contact with ambient air. In such cases, malleus, incus and the tympanic membrane are lost and the eustachian tube is shut so that extreme hardness of hearing is inevitable. Faced with such heavy impairments, conventional surgery often was of no avail.

The invention aims to providing help especially in such cases deemed rather hopeless up to now. Where the patient's inner ear and the auditory path still function, it is possible to implant a middle ear prosthesis and to couple it to the inner ear. Moreover, the prosthesis may be implanted if the middle ear failed to develop due to embryonic harm but the inner ear is working. Finally victims of accidents may be equipped with the prosthesis as long as inner ear and auditory path still operate.

It is an important object of the invention to create reliable aiding means for patients whose inner ear is intact yet whilst their middle ear is deficient or non-operative. It is further contemplated to also utilize the invention in less severe cases of failure and with domestic animals, provided they are mammals. As a solution to the problem posed, the invention provides a middle ear prosthesis with the features of the hereinafter set forth.

The principle of the invention comprises the surgical implantation of a complete middle ear prosthesis. This does away, in a surprisingly simple manner, with difficulties that could not be overcome in the past. As an entity, the novel middle ear prosthesis includes a confined volume within artificial walls of a premanufactured casing that is adapted to be dismantled following a performance check, to be transported, to be mounted stepwise and to provide a complete acoustical transmission system. It is free of living tissue within. No part of the implanted prosthesis will be exposed to the exterior.

The middle ear prosthesis features four main components or units. Adjacent the inner ear in the region of the oval window, there is an inner coupling unit. Next thereto a cover unit serves to confine a small volume of gas at the round window. Outwardly, a transfer unit is provided having an artificial tympanic membrane and a connection to a mastoid unit with a soft outside as well as a spongy damping insert. Thus the middle ear prosthesis according to the invention is a complete device for acoustical transmission as well as pressure balance. This is a considerable advance over the prior art which more or less successfully permitted, subject to available anchoring structures, to merely repair or replace individual pieces or elements of the oscillatory system. As a result, the restoration of hearing capability depended largely on chances and on sundries such as the surgeon's dexterity or the progress of healing.

An important feature is the connection to the oval window by means of a pipe socket, a sealing sleeve and a diaphragm which latter preferably includes central stiffening means functioning as stapes and simultaneously as an element of the oscillatory transmission system.

The cover unit includes a cap affixed in front of the round window. If required, a conduit may be provided for connection to the interior of the transfer unit.

The design of the transfer unit includes, between the tympanic membrane and the diaphragm an impedance converter or transducer which, comprises a transmission element or a transmission chain including vibratory elements that may be damping and be interconnected by adjustable coupling means. From ambience to the interior, the pressure is intensified at a ratio between 1:7 and 1:30 or above, especially wherein the oscillatory system has a large receiving face at the tympanic membrane and is suitably connected to a small force output face at the diaphragm, e.g. by an adhesive spring.

If an outer vibratory system is tuned to a lower frequency and an inner vibratory system is tuned to a higher frequency, the plotted area of the audiogram will closely approach that of a healthy ear, since the centers of the resonance ranges are superposed to harmonize.

Complete implantation using biocompatible materials is important whereby all of the prosthesis is imbedded in the patient's body tissue so that reactions of repulsion are precluded to the utmost.

The mastoid unit has a soft membrane outside that may be partly permeable to air which is useful where venting will be required at the mucous window. The rear wall of the mastoid unit, by contrast, is stiffer but nonetheless adapted to yield somewhat so as to suit a wide variety of topical conditions met with the individual patients. Further, hearing capability is much enhanced if the mastoid unit and the transfer unit are connected by a detachable junction for acoustical transmission. Preferably, a check valve is provided to fend off acoustic shocks and pressure waves.

At least the components that are immediately adjacent the inner ear may be secured by means of an adhesive paste permitting ingrowth of living cells which form a sort of interpenetrating trestle work. At the same time, the interior of the prosthesis and in particular that of the transfer unit will remain free of tissue.

Elastic straps serve to exactly center and fix the pipe socket and/or the diaphragm relative to the inner ear windows.

Further features, details and advantages of the invention will become evident from the wording of the claims and from the following disclosure elucidated by the drawings wherein:

FIG. 1 is a schematized head sectional view showing the mucous membrane of the middle ear, the section plane corresponding to the line I—I of FIG. 1a.

FIG. 2 shows a like head sectional view,

Figure 3:
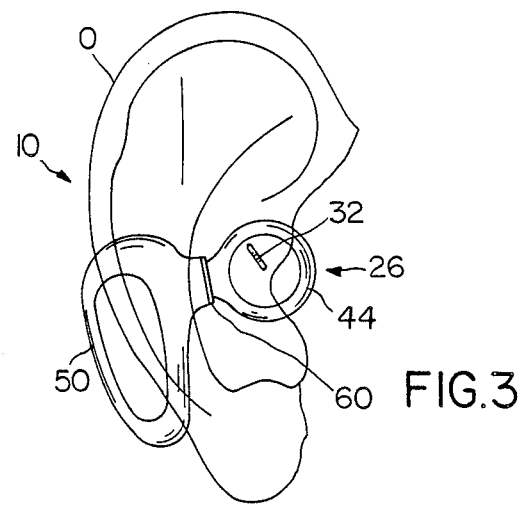
Figure 4:
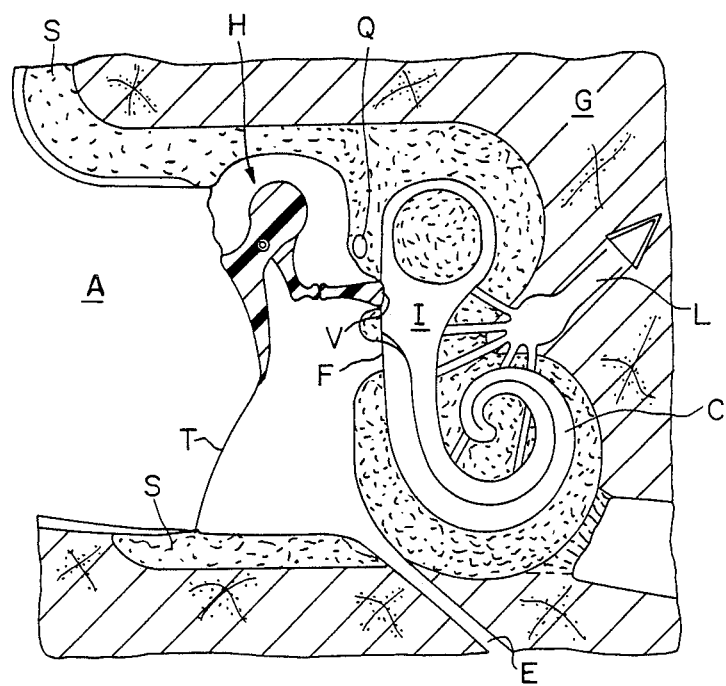
Figure 5:
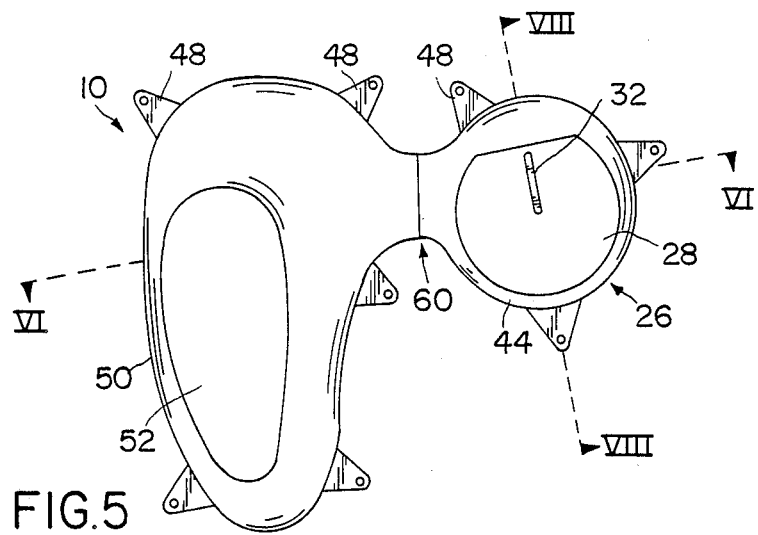
Figure 7:
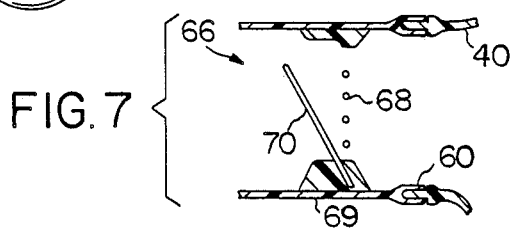
Figure 6:
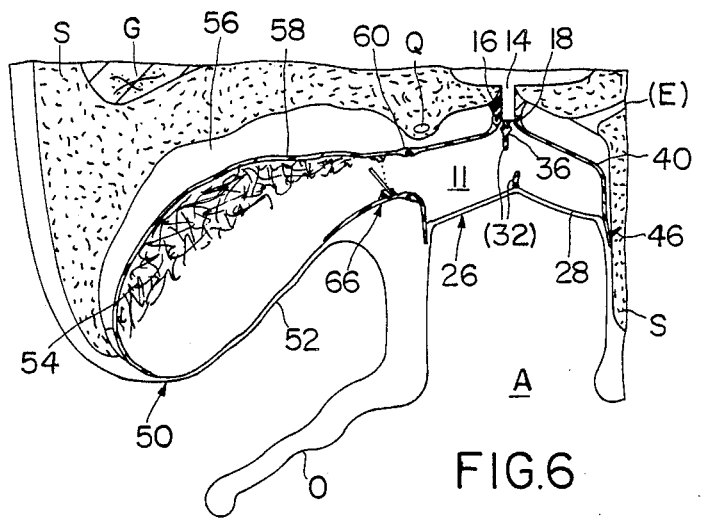
Figure 8:
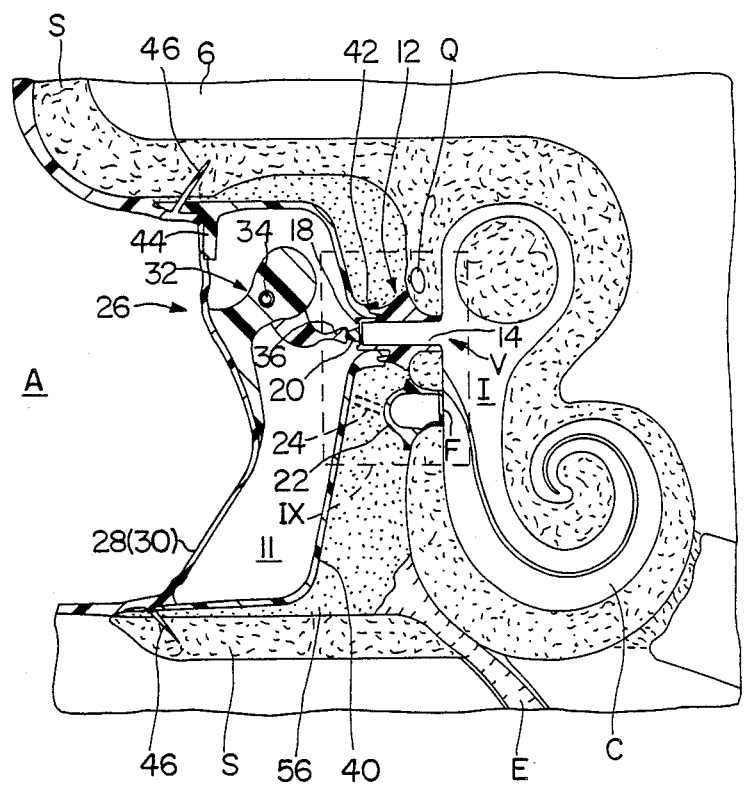
Figure 10:
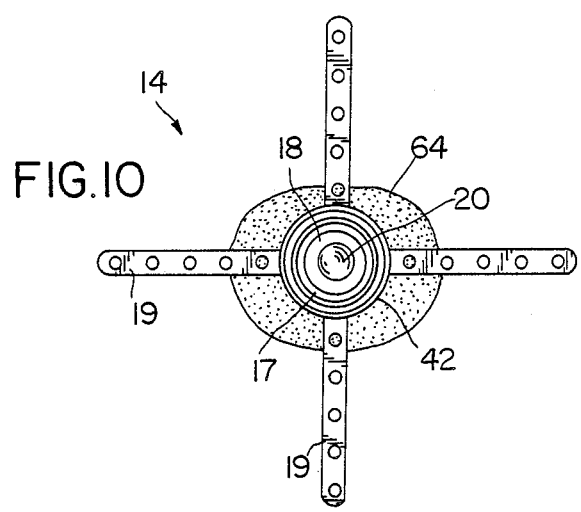
Figure 9:
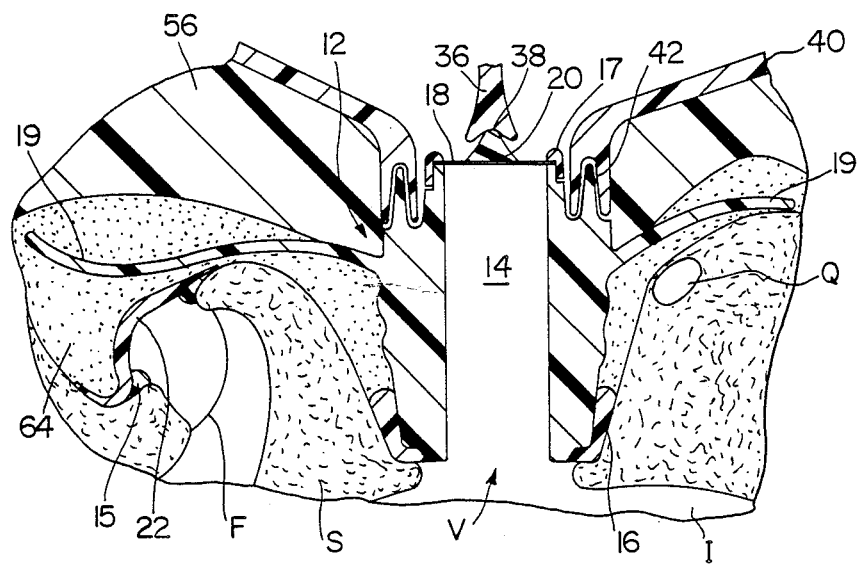
Figure 11:
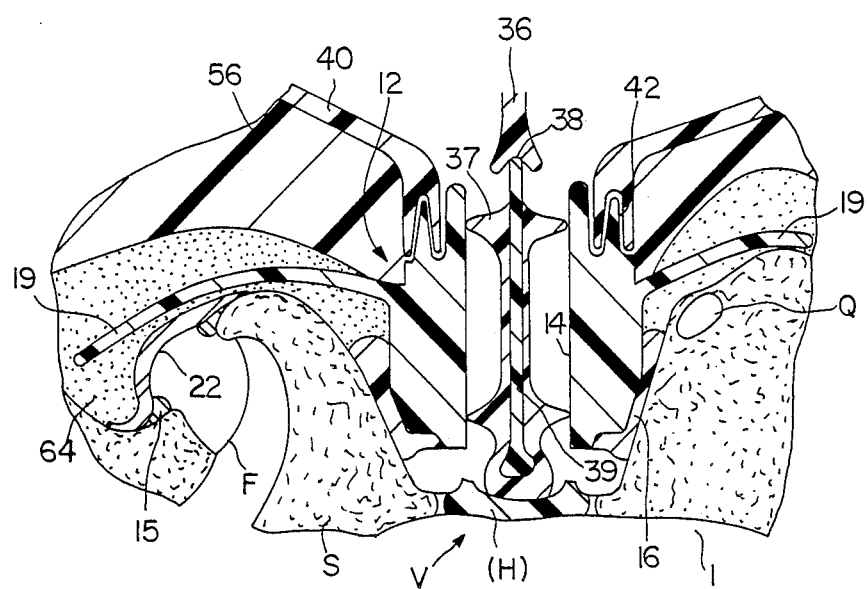

FIG. 3 is a view of the position of a prosthesis according to the invention relative to the auricle, FIG. 4 is an enlarged sectional view of a schematized middle ear structure, FIG. 5 is a front view of a middle ear prosthesis according to the invention, FIG. 6 is a cross sectional view of an implanted middle ear prosthesis, the section plane corresponding roughly to the line VI—VI in FIG. 5, FIG. 7 shows a much enlarged sectional view of a check valve, FIG. 8 is an enlarged diagrammatical sectional view of an implanted middle ear prosthesis, the section plane corresponding roughly to the line VIII—VIII in FIG. 5, FIG. 9 is a much enlarged sectional view of a schematized coupling unit of a prosthesis corresponding to the region IX shown with broken lines in FIG. 8, FIG. 10 is a view, also much enlarged, of a pipe socket and strap arrangement, and FIG. 11 shows a sectional view, similar to FIG. 9, of a modified coupling unit.

The illustrations of FIGS. 1 to 3 serve to elucidate the problem on hand. FIG. 1a shows a top view of a head K the nose N of which is indicated for proper orientation. The angled section of planes I—I lead behind the outer ear the auricles of which are marked by O.

In the lefthand portion of FIG. 1, a middle ear in good health is seen, including the mastoid cavity M whose interior is connected to the nasopharynx P via the Eustachian tube E. The brain G is schematized. In the righthand portion of FIG. 1, a middle ear disease is evident from the swollen mucous membrane that caused narrowing of the eustachian tube.

A suppuration condition in which the Eustachian tube is completely shut is seen in the righthand portion of FIG. 2. In order now to forestall damage to the inner ear and to restore or provide hearing capability, all of the inflamed tissue is removed and the middle ear prosthesis 10 according to the invention is implanted, as shown schematically in the lefthand portion of FIG. 2. It will be realized that a transfer unit 26 is connected to a mastoid unit 50 placed in the mastoid cavity M.

FIG. 3 shows the arrangement of the prosthesis 10 relative to an auricle O.

The schematic view of FIG. 4 will assist in understanding the function of the prosthesis 10. The middle ear structure includes the external auditory meatus A joined by the tympanic membrane T whose edges have grown into the tissue of the cranial bone S. Oncoming sound is transmitted with pressure boosting (at a static ratio of 1:22) to the stapedial footplate via a lever system H comprising malleus, incus and stapes which latter delivers acoustic oscillations to the oval window V and thus to the inner ear liquids I. The membrane of the round window F seals the cochlea C of the inner ear relative to the tympanic cavity, i.e. the interior of the middle ear. The auditory nerve L leads into the brain G.

Principally similar is the middle ear prosthesis 10 according to the invention. Its topical arrangement is seen in FIG. 5, whereas details will be evident from FIGS. 6 to 11. The prosthesis 10 comprises a coupling unit 12 having a pipe socket 14 as well as a sealing sleeve 16 which is preferably made of polytetrafluorethylene and is closed by means of a diaphragm 18 attached with a ring 17 (FIGS. 8 and 9). Artificial stapes 20 by way of a central reinforcement is arranged at the center of the diaphragm 18. For centered fixation, in particular, straps 19 (FIG. 10) are provided which may be integral with the pipe socket 14 and which may be anchored, for example, using a paste 64 of bone-dust and fibrin adhesive. The round window F is covered by a cap or cover unit 22. As indicated by broken lines in FIG. 8, a conduit 24 towards the transfer unit 26 may be provided.

The transfer unit 26 is a main component of the middle ear prosthesis 10. It includes an artificial tympanic membrane 28 having a large receiving face 30 from where a lever system 32 (FIG. 8) that comprises an axis of rotation 34 as well as a socket 36 provides connection via a small adhesive spring 38 to the artificial stapes 20 of the diagraphm 18 (see FIG. 9).

The interior 11 of the prosthesis 10 is confined by an inside wall 40 that is connected to the coupling unit 12 by a connection 42 which preferably is of a form-fitting or bonding nature. The volume between the inside wall 40 and the cranial bone S as well as the elements of inner ear and coupling unit includes a filling 56 of biocompatible material. The eustachian tube E is closed, too.

Whilst the connection 42 provides tight sealing towards the inner ear, the transfer unit 26 is secured outwardly by a frame 44 engaging the artifical tympanic membrane 28. Fixation is effected by means of pins 46 of biocompatible material which extend through tongues 48 (FIG. 5) and which are anchored in the cranial bone S. All of the outer surface is coated by thin epithelium (see FIGS. 6 and 8).

A detachable junction 60 serves to connect the transfer unit 26 with the mastoid unit 50. The latter includes, towards the auricle O, a soft membrane 52 also epithelialized and adapted to follow slow pressure variations. Since topical conditions widely vary with the individual patients, the rear wall 58 of the mastoid unit 50 is flexible to some extent so that fitting it is easier. If ambient pressure should rise, the soft membrane 52 will be forced inwardly until the pressure level is the same both within and outside the prosthesis 10. As ambient pressure decreases, the soft membrane 52 will automatically bulge again until the pressure levels are balanced. Therefore, such slow pressure fluctuation will not influence the acoustic system. A safeguard against sudden transient pressures of large differential is a check valve 66 provided at the junction 60 which preferably is plug-like. The check valve 66 includes a wide-mesh grid or screen 68 and on one side a resilient flap 70 (FIG. 7) adapted to shut off the interior 11 of the transfer unit 26 in respect of the mastoid unit 50. A damping insert 54 that partly fills the volume of the mastoid unit 50 is adjacent its rear wall 58, as will be seen in FIG. 6 where the lever system 32 (omitted here) of the transfer unit 26 is shown by broken lines only.

As compared to FIG. 9, a slightly modified embodiment of a coupling unit 12 is shown in FIG. 11. It will be utilized where the stapedial footplate of the natural system is intact yet and should be retained in order to prevent an infection hazard to the inner ear. This footplate is suspended by a ring gripping (Lig. annulare) and itself forms a sealing membrane so that no artificial partition will be required. The socket portion 36 will then drive, again preferably by means of an adhesive spring 38, a plunger 39 adapted to be axially shifted within the pipe socket 14, with a foot of the plunger engaging the stapedial footplate. Plunger 39 may be guided and possibly also sealed in the pipe socket 14 by collars 37 functioning as pistons, flanges or the like.

The walls of the middle ear prosthesis 10 preferably consist of rigid biocompatible material such as polytetrafluorethylene or titanium having a coat of biocompatible ceramics. A similar compound structure, though very thin, may also be provided for the artificial tympanic membrane 28. For coupling components, in particular, polytetrafluoroethylene or a similar material will be suitable. Attachment can be done by a fibrin adhesive, possibly with the addition of bone-dust gained from the patient as in the case of the adhesive paste 64. This will be applied both at the sealing sleeve 16 and at the cap 22 which may include a packing ring 15. The vibrating component parts of the transfer unit 26 may be attenuated by a suitable plastics coating.

Owing to its very small overall dimensions, the prosthesis 10 according to the invention may have a mass of about 0.5 g only. The impedance converter in the transfer unit 26 may be designed such that the maximum sensitivity centers on frequencies in the range from about 1,000 Hz to 4,000 Hz, in particular 3,500 Hz.

The application of the invention is not limited to ossical repair or replacement in the field of human medicine. Rather, the prosthesis can also be employed with domestic animals having a similar basic ear structure, e.g. horses, dogs, cats, etc.

All and any of the features and advantages of the invention, inclusive of design details and of spatial arrangements, as evident from the claims, from the specification and from the drawings may be inventionally substantially both per se and in most variegated combinations.

I claim:

1. A non-electromagnetic middle ear prosthesis for restoring and providing hearing capability for patients having suffered damage to their invivo sound conducting structures, which prosthesis is entirely mechanical and includes an enclosed outer casing defining a confined interior, the interior of said casing comprising four units, including:
  a coupling unit adapted to be coupled adjacent the oval window, said coupling unit including means for allowing mechanical transmission of acoustic oscillations to the oval window;
  a transfer unit including an artificial tympanic membrane spaced a distance from the coupling unit and defining an interior volume and a lever means disposed between the tympanic membrane and the oval window wherein the lever means delivers acoustic oscillations from the tympanic membrane to the oval window;
  a mastoid unit adapted to be connected to the transfer unit, said mastoid unit defining a predetermined volume filled with a dampening means and including a soft membrane for venting air wherein the combination of the soft membrane and the dampening means allows for automatic adjustment of pressure changes within the mastoid unit; and
  a cover unit adjacent the coupling unit and configured to cover the round window of the inner ear for maintaining a volume of gas outside the round window.

2. A prosthesis according to claim 1 wherein said coupling unit (12) comprises a tubular socket (14) including means to connect the socket (14) to the oval window (V) of the inner ear, a sealing sleeve (16) attached to an outer surface of said socket (14) and a diaphragm (18) disposed on said socket (14).

3. A prosthesis according to claim 2 wherein central stiffening means are provided which are coupled to the diaphragm (18) and to an artificial stapes (20).

4. A prosthesis according to claim 2 wherein a plunger (39) is disposed in the socket (14) and is adapted for axial displacement therein, said plunger (39) having collars (37) for guiding and sealing the plunger in the pipe socket and the plunger (39) has a foot for engaging the stapedial footplate.

5. A prosthesis according to claim 2 wherein said cover unit (22) includes a cap configured for attachment to said round window (F).

6. A prosthesis according to claim 2 wherein said cover unit (22) includes a conduit (24) for connection to the interior of the transfer unit (26).

7. A prosthesis according to claim 2 wherein the transfer unit 26 includes an impedance converter arranged between the tympanic membrane (28) and the diaphragm (18).

8. A prosthesis according to claim 7 wherein the impedance converter comprises transmission means a chain including at least one vibratory element (28 to 36, 20) made of a biocompatible material.

9. A prosthesis according to claim 8 wherein each vibratory element is coated with a bicompatible plastic for attenuation.

10. A prosthesis according to claim 8 wherein means include members forming a transmission chain and said members being said transmission (20, 28 to 36) interconnected by adjustable coupling means.

11. A prosthesis according to claim 7 wherein said impedance converter is designed for pressure intensification from ambience to the interior at a ratio of at least 1:7 to 1:30.

12. A prosthesis according to claim 8 wherein said transmission means (20, 28–36) includes a system of coupled oscillators, said system including a large receiving face (30) adjacent the tympanic membrane (28) and connectors means for positive connectors to a small force output face of the diaphragm (18).

13. A prosthesis according to claim 12 wherein an adhesive spring (38) is provided for connection to said diaphragm (18).

14. A prosthesis according to claim 7 comprising outer and inner vibratory systems, the outer vibratory system being tuned to a lower frequency of about 1000 Hz and the inner vibratory system being tuned to a higher frequency of about 4000 Hz.

15. A prosthesis according to claim 7 wherein said transfer unit (26) includes a rigid inside wall and further includes sealing means adapted for detachable connection to said coupling unit (12).

16. A prosthesis according to claim 1 wherein the transfer unit (26) includes means for securing it to the adjacent bone (S) in particular such that the edges of the tympanic membrane (28) are attached to the adjacent bone by tongues (48) and by pins (46) of biocompatible material.

17. A prosthesis according to claim 1 wherein the transfer unit (26) includes a frame (44) of at least approximately annular shape for holding the tympanic membrane (28) to proven position.

18. A prosthesis according to claim 17 wherein at least an outer wall that forms the tympanic membrane (28) and a pressure balancing component (52) are adapted to be epithelialized.

19. A prosthesis according to claim 1 wherein the tympanic membrane (28) is a flat cone directed inwardly and is of titanium sheet with a biocompatible coating.

20. A prosthesis according to claim 1 wherein the mastoid unit (50) includes a soft outer membrane (52).

21. A prosthesis according to claim 20 wherein the soft membrane (52) is at least partly permeable to air.

22. A prosthesis according to claim 20 wherein the mastoid unit (50) includes a resiliently yielding rear wall (58).

23. A prosthesis according to claim 20 wherein detachable junction means (60) are provided between the mastoid unit (50) and the transfer unit (26) for acoustical connection therebetween.

24. A prosthesis according to claim 23 wherein a check valve (66) is provided between the mastoid unit (50) and the transfer unit (26).

25. A prosthesis according to claim 24 wherein the check valve (66) is adjacent the detachable junction means (60) and includes a grid (68) as well as a flap (70).

26. A prosthesis according to claim 4 wherein adhesive paste means (64) adapted for ingrowth of connective tissue cells are provided for securing at least those components that are immediately adjacent the inner ear.

27. A prosthesis according to claim 4 wherein flexible strap means (19) are provided for centering and attachment of the socket (14) and the diaphragm (18).

* * * * *